United States Patent [19]
Widinski et al.

[11] Patent Number: 4,700,943
[45] Date of Patent: Oct. 20, 1987

[54] EXERCISING DEVICE

[75] Inventors: Paul R. Widinski, Arvada; Glenn N. Taylor, Longmont, both of Colo.

[73] Assignee: Health and Home Products, Longmont, Colo.

[21] Appl. No.: 732,832

[22] Filed: May 10, 1985

[51] Int. Cl.$^4$ ............... A63B 23/04; A63B 21/12
[52] U.S. Cl. ............................. 272/96; 272/119
[58] Field of Search ................... 272/119, 96, 93; 273/54 B, 55 B; 128/400, 402, DIG. 20, DIG. 24; 441/56, 58, 61

[56] References Cited

U.S. PATENT DOCUMENTS

| | | | |
|---|---|---|---|
| 3,348,842 | 10/1967 | Stern | 273/55 B |
| 4,322,072 | 3/1982 | White | 272/119 |
| 4,355,801 | 10/1982 | Thomsen | 272/119 |
| 4,357,009 | 11/1982 | Baker | 272/119 |
| 4,405,129 | 9/1983 | Stuckey | 272/96 |

FOREIGN PATENT DOCUMENTS 509276 7/1939 United Kingdom ............... 272/119

Primary Examiner—Richard J. Apley
Assistant Examiner—H. Macey
Attorney, Agent, or Firm—Powell L. Sprunger

[57] ABSTRACT

An exercising device for the foot comprising, an instep portion for covering an upper portion of the foot having a pair of flexible sheets defining a closed chamber to receive a weight medium, with the instep portion extending from a location adjacent the toes to a location adjacent the ankle, and having a pair of side portions extending around opposed sides of the foot and defining a pair of opposed side edges, with the instep portion having a pair of opposed ends extending toward the ankle on opposed sides of the foot. The exercising device has a closable access associated with the instep portion to place a weight medium in the chamber. The exercising device has a sole strap extending between the opposed sides of the instep portion for placement beneath the foot, with the instep portion and sole strap defining a first opening to receive the toes, and a second opening to receive the heel. The exercising device has a pair of opposed ears extending from the ends of the instep portion toward the ankle, and a device for securing the ears about the ankle.

10 Claims, 6 Drawing Figures

EXERCISING DEVICE

BACKGROUND OF THE INVENTION

The present invention relates to exercising devices.

In the past, exercising devices in the form of sand or metal filled weights have been attached at a location above the ankle. However, it is desirable to increase the resistive effect of an equivalent weight above the ankle. It is also desirable to select the amount of resistive effect of the device. Further, it is desirable to provide therapeutic effects of the device to the body, such as providing heat or coldness to the body.

SUMMARY OF THE INVENTION

A principal feature of the present invention is the provision of an improved exercising device.

The exercising device of the present invention comprises, an instep portion for covering an upper portion of the foot comprising a pair of flexible sheets defining a closed chamber, with the instep portion extending from a location adjacent the toes to a location adjacent the ankle, and having a pair of side portions extending around opposed sides of the foot and defining a pair of opposed side edges, with the instep portion having a pair of opposed ends extending toward the ankle on opposed sides of the foot. The exercising device has closable access means associated with the instep portion, and a sole strap extending between the opposed sides of the instep portion for placement beneath the foot, with the instep portion and sole strap defining a first opening to receive the toes, and a second opening to receive the heel. The exercising device has a pair of opposed ears extending from the ends of the instep portion toward the ankle, and means for securing the ears about the ankle.

A feature of the present invention is that a weight medium may be placed into the chamber through the closable access means.

Another feature of the invention is that a selected quantity of the weight medium may be placed in the chamber.

A further feature of the invention is that the exercising device may be secured about the foot for the purpose of stressing the joints or muscles to strengthen or rehabilitate the required area.

Yet another feature of the invention is that the hand may be placed in the exercising device, and may be utilized to exercise the hand and arm.

Further features will become more fully apparent in the following description of the embodiments of this invention and from the appended claims.

DESCRIPTION OF THE PREFERRED EMBODIMENTS

Figure 1:
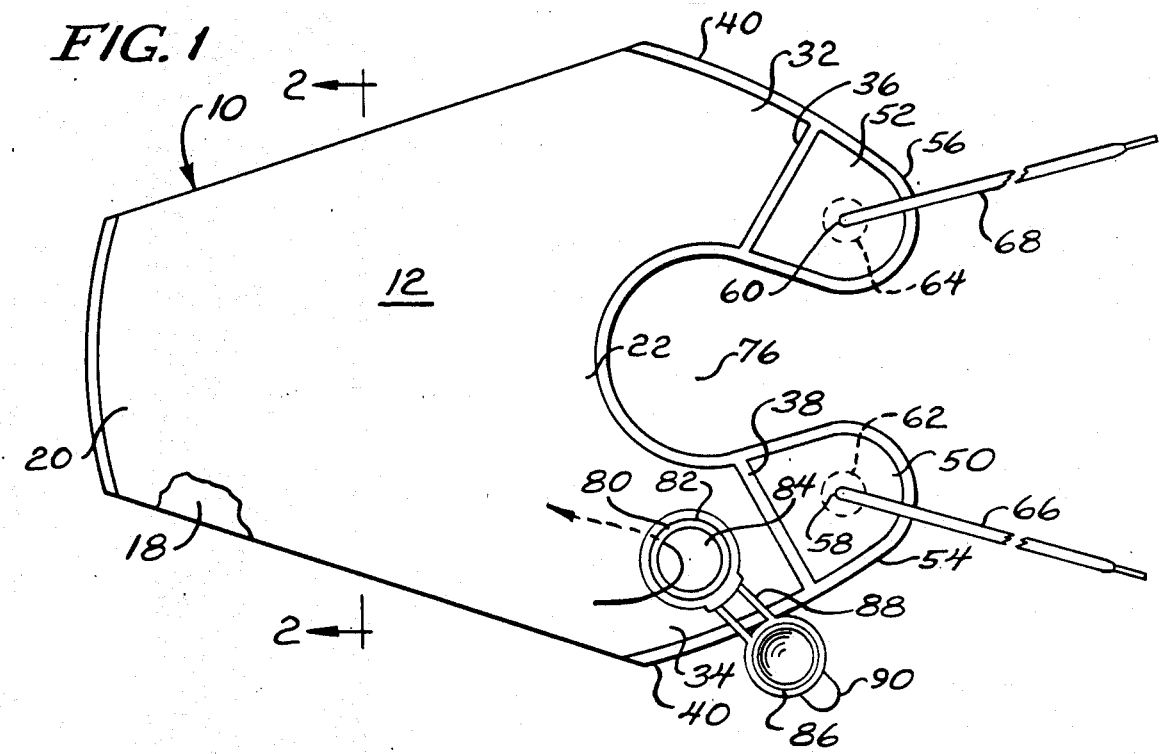
FIG. 1 is an upper plan view of an exercising device of the present invention.
Figure 2:
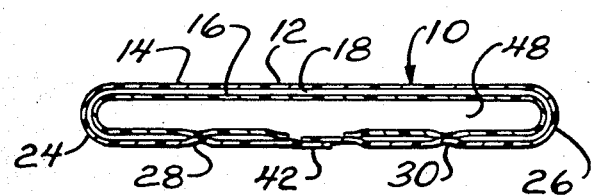
FIG. 2 is a sectional view taken substantially as indicated along the line 2—2 of FIG. 1.
Figure 3:
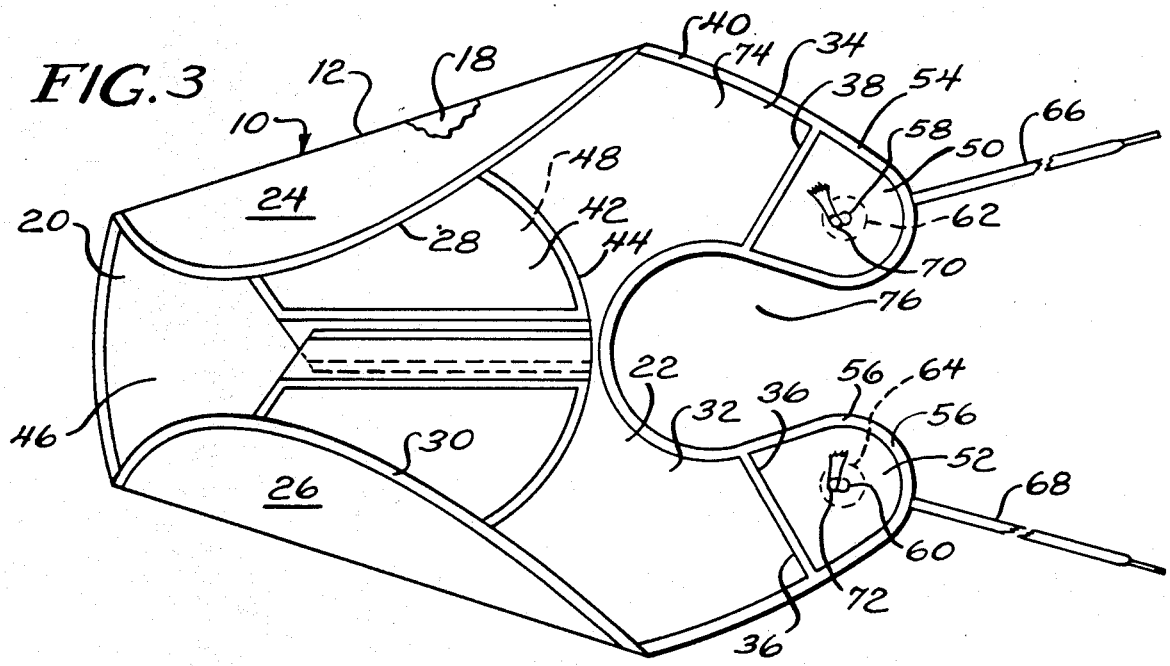
FIG. 3 is a lower plan view of the exercising device of FIG. 1.

Referring now to FIGS. 1-3, there is shown an exercising device generally designated 10 for use in exercising the foot or hand as will be seen below, although for convenience the device 10 will be described primarily for use on the foot. The device 10 has an instep portion 12 for covering an upper portion of the foot comprising an upper sheet 14 of liquid impervious material, and a lower sheet 16 of liquid impervious material. The sheets 14 and 16 may be made from a suitable flexible plastic material, such as polypropylene. The sheets 14 and 16 also define a closed chamber 18 to receive a weight medium, as will be discussed below. The instep portion 12 has a distal portion 20 located adjacent the toes when placed on the foot, and the instep portion 12 extends to a proximal portion 22 which is located adjacent the ankle when the device 10 is placed on the foot. The instep portion 12 has a pair of opposed side portions 24 and 26 extending around the sides of the foot when the device 10 is placed on the foot, with the side portions 24 and 26 defining a pair of opposed side edges 28 and 30 of the instep portion 12. The instep portion 12 also has a pair of opposed ends 32 and 34 extending toward the ankle on opposed sides of the foot when the device 10 is placed on the foot. As shown, the ends 32 and 34 have seal lines 36 and 38 defining ends of the chamber 18 of the instep portion 12. The instep portion 12 also has a seal line 40 of the sheets 14 and 16 extending from the seal lines 36 and 38 around the side edges 28 and 30 and the distal portion 20 in order to close the chamber 18 of the instep portion 12.

The device 10 has a sole strap 42 of suitable flexible plastic material, such as polypropylene, extending between the side edges 28 and 30 of the instep portion 12 for placement beneath the foot when the device 10 is placed on the foot. As shown, the sole strap 42 may have an arcuate portion 44 which is directed toward the heel when the device 10 is placed on the foot. The instep portion 12 extends to a location further adjacent the toes than the sole strap 42. The instep portion 12 and sole strap 42 define an opening 46 to receive the toes, and the instep portion 12 and sole strap 42 define a channel 48 to receive the foot or hand.

The instep portion 12 and sole strap 42 also define an enlarged opening 74 to receive the heel of the user when the device 10 is placed on the foot. Also, the instep portion 12 and ears 50 and 52 define an arcuate cut-out 76 in order to receive the forward portion of the ankle when the device 10 is placed on the foot. If desired, the sole strap 42 may be made of a single or double layer of the plastic material.

The device 10 has a pair of opposed ears 50 and 52 extending from the ends 32 and 34 of the instep portion 12 toward the ankle when the device 10 is placed on the foot. The ears 50 and 52 may comprise a pair of sheets which extend from the sheets 14 and 16, with the sheets being sealed and closed along lines 54 and 56, and along the previously described seal lines 36 and 38 associated with the instep portion 12.

The ears 50 and 52 have a pair of apertures 58 and 60 extending through the sheets of the ears 50 and 52. In a preferred form, the device 10 has a pair of grommets 62 and 64 between the sheets of the ears 50 and 52 and having apertures in alignment with the apertures 58 and 60 of the ears 50 and 52, with the grommets 62 and 64 being secured in this location.

The device 10 has a pair of ties 66 and 68 having enlarged portions, such as knots 70 and 72, to prevent passage of the ties 66 and 68 through the apertures 58 and 60. Thus, as shown, the knots 70 and 72 are located on the underside of the ears 50 and 52, and the ties 66 and 68 extend through the apertures 58 and 60 for a substantial distance on the other side of the ears 50 and 52.

The device 10 has closable access means 80 associated with the instep portion 12 in order to place the weight medium in the chamber 18. In a preferred form, the access means 80 is located adjacent one of the ends 34 of the instep portion 12. The access means 80 comprises an annular rim 82 secured to the upper sheet 14 of the instep portion 12 and located over an opening 84 of the upper sheet 14. The access means 80 has a plug 86 which may be releasably received in the rim 82 in order to close the access means 80, or the plug 86 may be removed from the rim 82 in order to open the access means 80. In the preferred form, the access means 80 has a strap 88 which connects the plug 86 to the rim 82. The access means 80 may be made from a suitable plastic material, and the plug 86 may have an outwardly directed tab 90 to facilitate removal of the plug 86 from the rim 82.

Figure 4:
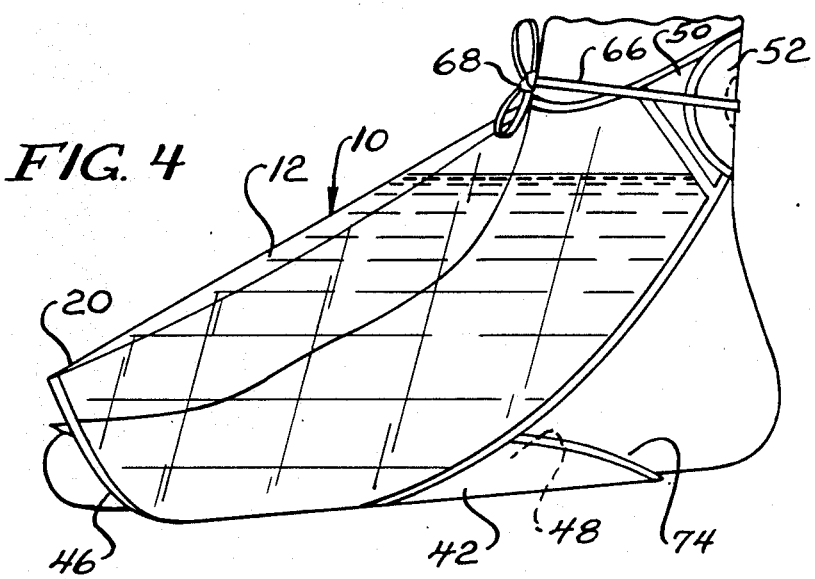
FIG. 4 is a perspective view illustrating use of the exercising device on the foot.

In use on the foot, with reference to FIG. 4, the chamber 18 is filled through the access means with a weight medium to a desired extent, and the device 10 is placed on the foot in the following manner. The foot is inserted through the channel 48 with the instep portion 12 located above the foot, and the sole strap 42 located beneath the foot, in a position with the toes extending through the distal opening 46, and the heel located in the opening 74. The ears 50 and 52 of the device 10 are located adjacent the back of the ankle, and the ties 66 and 68 are crossed on the back of the ankle. The ties 66 and 68 are tied together adjacent the front of the ankle in order to retain the device 10 in place on the foot. Of course, the ears 50 and 52 need not have sufficient length to cross behind the ankle, in which case the ties 66 and 68 have sufficient length to extend from the ears 50 and 52 about the ankle with the ties crossing in back of the ankle.

Figure 5:
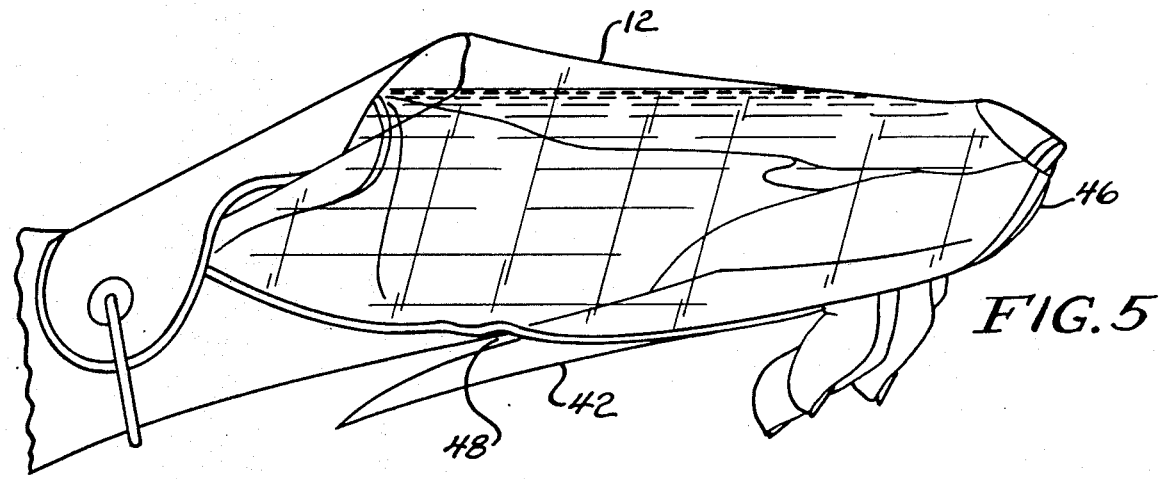
FIG. 5 is a perspective view illustrating use of the exercising device on the hand.

In use of the device for the hand, with reference to FIG. 5, the hand is inserted through the channel 48 with the instep portion 12 located above the hand, and the sole strap 42 located beneath the hand. The fingers of the hand are placed through the opening 46, and the fingers grip the distal portion of the sole strap 42 in order to exercise the hand and arm.

As will be seen, the device 10 conforms to the shape of the foot or hand to provide a resistive weight to stress the joints or muscles being exercised to strengthen or rehabilitate the required areas. The chamber 18 may be filled with warm or cold water to provide a therapeutic effect, and as the bag is moved during the exercise the flow of liquid also provides a gentle massaging action to the area which is covered by the device 10. Although the device 10 is designed primarily for use in connection with liquids in the chamber 18, it may also be filled with a solid material, such as salt or sand to provide more weight. Due to the position of the weight of the device 10 when used on the foot area, it provides more resistive weight than an equivalent weight worn above the ankle which may be filled with sand or metal weights. This feature is a function of the leg length and distance from the top of the ankle to the top of the toe area, but on the average the liquid weight in the chamber 18 should be 20% to 25% greater resistive weight.

When utilized in a rehabilitative circumstance, this device allows the therapist to achieve greater resistance without being restricted to multiples of a given weight. Due to the design of the device 10, it is possible to vary the weight from light to medium by increasing the content of the chamber 18. This provides the user or therapist more latitude in designing the strengthening or rehabilitative programs. Further, the normal use of the device 10 automatically provides an exercising effort to the ankle area and causes the upper foot muscles to be extended, which would be beneficial to multiple-sclerosis victims.

The device 10, which is capable of being filled with a common fluid, such as water, can be emptied and taken with the user for travelling purposes in a light and convenient fashion. The device 20 permits the user to maintain his exercise program in almost any location and environment. As previously indicated, the device may be heated or cooled to provide a therapeutic effect to the user. This can be accomplished in conjunction with an exercise program to use the device 10 as a simple hot or cold pack. The device 10 may be filled with hot or cold material or depending on the contents it may be filled and brought to the desired temperature by placing it in a refrigerator or pan of heated water. If the contents are inert solids, the contents may also be warmed by placing the entire filled device 10 in a microwave oven for a short period of time. If a liquid or less than the full amount of solids are used in the chamber 18, the device 10 provides a gentle massaging effect as the area being exercised is moved. This effect is due to the changing levels of weight over each area as the contents are shifted during the exercise. This effect is enhanced by the use of a liquid content which also generates a wavelike pulse passing over the covered areas.

Figure 6:
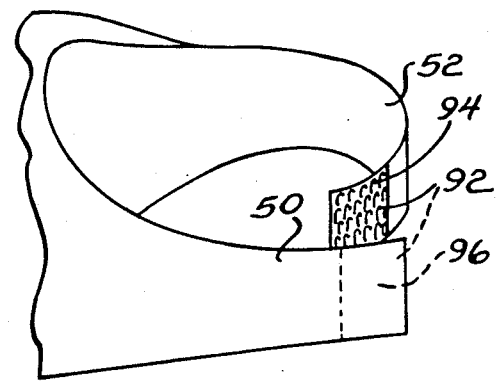
FIG. 6 is a fragmentary perspective view of another embodiment of the present invention.

Another embodiment of the present invention is illustrated in FIG. 6, in which like reference numerals designate like parts. In this embodiment, the ears 50 and 52 have a sufficient length to extend around the back of the ankle. The ears 50 and 52 have fastening means 92 for securing the ears 50 and 52 together about the ankle in order to secure the device 10 in place on the foot. In a preferred form, the fastening means 92 comprises a hook strip 94 and a loop strip 96 which may be releasably secured together about the back of the ankle.

The foregoing detailed description is given for clearness of understanding only, and no unnecessary limitations should be understood therefrom, as modifications will be obvious to those skilled in the art.

We claim:

1. An exercising device for the foot or hand, comprising;
    an instep portion adapted to cover the upper portion of the foot comprising a pair of flexible sheets defining a closed chamber to receive a weight medium, said instep portion adapted to extend from a location adjacent the toes to a location adjacent the ankle, and having a pair of opposed side portions adapted to extend around opposed sides of the foot and defining a pair of opposed side edges, one extremity of said instep portion having a curved configuration thereby defining a pair of opposed ends, each being in fluid communication with said chamber and adapted to extend toward the ankle on opposed sides of the foot;

closable access means associated with the instep portion to place the weight medium in said member;

a sole strap extending between the opposed sides of the instep portion adapted to be placed beneath the foot, said instep portion and sole strap defining a first opening adapted to receive the toes, and a second opening adpated to receive the heel;

a pair of opposed ears extending from the opposed ends of the instep portion, not in fluid flow communication with the opposed ends and adapted to extend toward the ankle; and means for securing the ears together adapted to secure the ears about the ankle.

2. The device of claim 1 in which the ears are adapted to overlap behind the ankle, and including means for fastening the ears together in overlapping relation.

3. The device of claim 2 wherein the fastening means comprises hook and loop fasteneing strips on the ears.

4. The device of claim 1 wherein the securing means comprises a pair of ties extending from an outer surface of each of the ears, said ties having a sufficient length adapted to be crossed behind the ankle and tied together at a location adjacent the front of the ankle.

5. The device of claim 1 wherein the access means comprises an annular rim secured to the instep portion over an opening in an outer sheet of the instep portion, and a plug releasably received in and closing the rim.

6. The device of claim 5 including a strap connecting the plug to the rim.

7. The device of claim 1 wherein the access means is located adjacent one of the opposed ends of the instep portion.

8. The device of claim 1 wherein the instep portion extends beyond the sole strap in both a forward and rearward direction.

9. The device of claim 1 wherein the sole strap has an arcuate configuration directed toward the opposed ends.

10. The device of claim 1 wherein the instep portion and ears define an arcuate cut-out adapted to receive the ankle.

* * * * *